(12) United States Patent  
Li et al.

(10) Patent No.: US 9,383,325 B2  
(45) Date of Patent: Jul. 5, 2016

(54) METHOD FOR DETERMINING GEOMETRIC RELATIONSHIPS OF CRYSTAL RECIPROCAL VECTORS ON TWO-DIMENSIONAL PLANES OBTAINED FROM SINGLE EBSD PATTERN

(71) Applicant: East China Jiaotong University, Nanchang, Jiangxi (CN)

(72) Inventors: Lili Li, Jiangxi (CN); Ming Han, Jiangxi (CN); Guangyao Xiong, Jiangxi (CN); Honglin Luo, Jiangxi (CN); Yizao Wan, Jiangxi (CN)

(73) Assignee: East China Jiaotong University, Nanchang, Jiangxi (CN)

( * ) Notice: Subject to any disclaimer, the term of this patent is extended or adjusted under 35 U.S.C. 154(b) by 0 days.

(21) Appl. No.: 14/993,664

(22) Filed: Jan. 12, 2016

(65) Prior Publication Data

US 2016/0123907 A1    May 5, 2016

(30) Foreign Application Priority Data

Aug. 3, 2015    (CN) .......................... 2015 1 0479250

(51) Int. Cl.
| | |
|---|---|
| *G01N 23/00* | (2006.01) |
| *G01N 23/207* | (2006.01) |
| *G01N 23/203* | (2006.01) |

(52) U.S. Cl.
CPC ............ *G01N 23/207* (2013.01); *G01N 23/203* (2013.01)

(58) Field of Classification Search
CPC ........................... G01N 23/207; G01N 23/203
USPC .................................................... 250/306, 307
See application file for complete search history.

(56) References Cited

U.S. PATENT DOCUMENTS 6,555,817 B1 * 4/2003 Rohde ...................... G21K 1/08  
250/311

* cited by examiner

*Primary Examiner* — Michael Maskell

(57) ABSTRACT

A method for determining geometric relationships of crystal reciprocal vectors on the two-dimensional planes obtained from an EBSD pattern includes steps of: geometrically correcting Kikuchi bands for obtaining the reciprocal vectors corresponding to the Kikuchi bands; selecting a set of reciprocal vectors which define a parallelogram with minimum area on the reciprocal plane as a two-dimensional basis for forming a grid, marking the basis; determining integer coordinates of other reciprocal vectors on the reciprocal plane relative to the basis, obtaining the deviations of the integer coordinates from the nearest grid nodes, marking the reciprocal vector with minimum deviation; fitting the length and the angel of the basis, redefining a new two-dimensional grid by the fitting result; repeating till all reciprocal vectors on the reciprocal plane are marked, wherein integer coordinates of the reciprocal vectors relative to the last two-dimensional basis now disclose the geometric relationships.

4 Claims, 4 Drawing Sheets

METHOD FOR DETERMINING GEOMETRIC RELATIONSHIPS OF CRYSTAL RECIPROCAL VECTORS ON TWO-DIMENSIONAL PLANES OBTAINED FROM SINGLE EBSD PATTERN

CROSS REFERENCE OF RELATED APPLICATION

The present invention claims priority under 35 U.S.C. 119(a-d) to CN 201510479250.2, filed Aug. 3, 2015.

BACKGROUND OF THE PRESENT INVENTION

1. Field of Invention

The present invention relates to the technical field of microstructure characterization of crystalline materials and crystallographic analysis, and more particularly to a method for determining geometric relationships of crystal reciprocal vectors on the two-dimensional planes obtained from an EBSD (electron backscatter diffraction) pattern.

2. Description of Related Arts

Most of the currently used materials belong to crystalline materials. The conventional methods for determining an unknown crystal lattice comprise XRD (x-ray diffraction) and SAED (selected-area electron diffraction). These two classic methods have own advantages and disadvantages. The former has higher accuracy for analyzed unit cell parameters and is capable of applying the diffraction intensity to further precisely position atomic coordinates in unit cells. However, it is unable to directly observe microstructure morphology inside the sample in real time, and generally needs that the sample consists of single phase. The latter allows the user not only to use electron diffraction to characterize crystallography of the microstructure at regions of interest, but also to directly observe the morphology of the microstructure in real time on the transmission electron microscope, which is the greatest advantage. Its disadvantage is more difficult to prepare the sample. Therefore, it is still a challenging work to simultaneously characterize unknown crystal lattice and its morphology of a bulk sample in practice, and especially lacking a convenient, fast and accurate method to determine lattices with low symmetry which commonly exist in minerals.

In recent twenty years, the EBSD technique has made great progress in the aspect of materials science research. EBSD is an accessory of SEM (scanning electron microscope), so that microstructure morphology of crystalline materials are able to be directly observed in real time, thereby advantages of the SAED are kept. More importantly, the EBSD is used on the SEM, so that the requirements for preparing the sample are greatly simplified. Up to now, all applications of the EBSD technique have been limited on the basis of orientation analyses of known crystals. Therefore, it is no doubt that the function of determining unknown lattices of bulk crystals using an EBSD pattern provides a new operating mode for SEM. The present invention is beneficial to achieve such a new function.

In general, an EBSD pattern comprises dozens of Kikuchi bands, in which the width of each Kikuchi band is relevant to the interplanar spacing in a crystal. By means of the PC (pattern center) and the DD (detector distance) of an EBSD pattern, the length and direction of a reciprocal vector corresponding to a crystallographic plane in direct space can be determined via the width and azimuth of the Kikuchi band. The Kikuchi bands in an EBSD pattern intersect into different Kikuchi poles which are equivalent to two-dimensional reciprocal planes of the crystal. Generally, there are hundreds of Kikuchi poles in a single EBSD pattern, simultaneously providing hundreds of two-dimensional reciprocal planes of the crystal. Therefore, an EBSD pattern of a crystalline sample reflects rich crystallographic information, which is the greatest advantage of the EBSD technique. Compared with other diffraction techniques, disadvantages of the EBSD technique are poor contrasts at edges of the Kikuchi bands and large errors of measurement data, wherein the errors of the PC and the DD usually reach more than 10%, and the measurement errors of the width of the Kikuchi bands reach 20% (reference: D. J. Dingley and S. I. Wright. *Determination of crystal phase from an electron backscatter diffraction pattern. J. Appl. Cryst.* 42(2009):234-241).

In recent years, the applicants of the present application have disclosed the determination of Bravais lattice of unknown crystals by means of single EBSD pattern in references comprising: *3D reconstruction for Bravais lattice of unknown crystals using EBSD pattern. Journal of Chinese Electron Microscopy Society*, December 2008, Vol. 27, No. 6; *3D reconstruction for Bravais lattice of hexagonal crystal using single EBSD pattern. Journal of Chinese Electron Microscopy Society*, August 2010, Vol. 29, No. 4; *Reconstruction for 3D reciprocal primitive cell of crystals using EBSD pattern. Paper collection of the second National Symposium on electron backscatter diffraction (EBSD) technology and application, the Sixth National Symposium on science and technology*, Dec. 31, 2007; and Chinese patent application No. 200810237624.X, filed on Nov. 25, 2008, Method for determining Bravais lattice of unknown crystals using electron backscatter diffraction.

According to the above published references, the applicants disclosed the determination of Bravais lattice of unknown crystals based on a single EBSD pattern, which means using a large amount of two-dimensional reciprocal planes revealed from a single EBSD pattern, reconstructing a three-dimensional reciprocal lattice according to the geometric relationships of crystal reciprocal vectors on the two-dimensional planes, transforming the reciprocal lattice into a direct lattice. Before the three-dimensional reconstruction, every two-dimensional reciprocal plane needs to be determined from the EBSD pattern, and especially, the geometric relationships of crystal reciprocal vectors on the two-dimensional reciprocal planes need to be correctly described. Therefore, the correct geometric relationships are the key to achieve the three-dimensional reconstruction. However, due to large errors of EBSD original measurement data, even after geometric correction and a least squares fitting, the vector distributions on the two-dimensional reciprocal planes are still unable to directly reflect inherent geometric relationships.

Aiming at the shortcomings of the published methods, the present invention is provided.

SUMMARY OF THE PRESENT INVENTION

Aiming at the shortcoming of the published methods, the present invention provides a new step-by-step fitting method, which is capable of determining inherently geometric relationships of crystal reciprocal vectors on the two-dimensional reciprocal planes under the circumstance of large errors.

Accordingly, the technical solution of the present invention is to provide a new method for determining geometric relationships of crystal reciprocal vectors on the two-dimensional planes obtained from an EBSD pattern, comprising steps of:

1) collecting an EBSD (electron backscatter diffraction) pattern of a crystalline sample on a SEM (scanning electron microscope), recording the PC (pattern center), the DD (detector distance) and the accelerating voltage of the EBSD pattern;

2) identifying a pair of edges at the narrowest location for each visible Kikuchi band, wherein a central line of the Kikuchi band is firstly determined, and then a pair of parallel lines are used to respectively match with the edges at the narrowest location of the Kikuchi band, such that a width of the Kikuchi band is represented by an interval between the pair of parallel lines, alternatively, using two parallel lines to directly match with the narrowest location of the Kikuchi band, then determine the central line according to the parallel lines;

3) geometrically correcting all the detected Kikuchi bands by the PC and the DD, obtaining the reciprocal vectors corresponding to the Kikuchi bands, and simultaneously transforming the central line of the Kikuchi bands into the trace line of the Kikuchi bands, wherein the step 3) specifically comprises sub-steps of:

3.1) determining L according to the DD and the EBSD pattern width, wherein $$L = (\text{pattern width}) \times DD,$$

wherein the L is a distance from a signal source to the PC of the EBSD pattern;

3.2) determining a position of the signal source according to the PC and the L;

3.3) according to the position of the signal source and the parallel lines respectively matching with the edges at the narrowest location of the Kikuchi bands, determining the angle $2\theta_i$ between planes $M_i$ and $N_i$, wherein after geometric correction, the width of the Kikuchi bands is $$w_i = 2L \tan(\theta_i),$$

the length of the reciprocal vectors is $$H_i = \frac{2}{\lambda}\tan(\theta_i);$$

and 3.4) determining the trace line of the Kikuchi bands according to the intersecting line formed by the bisector plane of planes $M_i$ and $N_i$ and the EBSD pattern plane;

4) according to the fact which all Kikuchi bands belonging to a zone axis must pass through a Kikuchi pole, obtaining all reciprocal vectors on each reciprocal plane;

5) calculating the area of all possible parallelograms defined by any two different reciprocal vectors on a two-dimensional reciprocal plane, selecting a set of reciprocal vectors with the smallest parallelogram area as a two-dimensional basis, setting the basis as marked reciprocal vectors on the reciprocal plane;

6) the two-dimensional basis defines a two-dimensional grid, in which the coordinates of other reciprocal vectors with respect to the basis on the reciprocal plane are able to be determined, and then obtaining deviations of ends of other reciprocal vectors from the nearest grid nodes;

7) selecting a reciprocal vector with the smallest deviation from all unmarked reciprocal vectors on the reciprocal plane, classifying the reciprocal vector with the smallest deviation into marked reciprocal vectors, and then fitting the lengths and the angle of the two-dimensional basis based on the ends and coordinates relative to the two-dimensional basis of all the marked reciprocal vectors, redefining a new two-dimensional grid by the fitting result;

8) obtaining the integer coordinates of unmarked reciprocal vectors on the reciprocal plane relative to the new two-dimensional basis, obtaining deviation of the ends of the unmarked reciprocal vectors from the nearest grid nodes; and 9) repeating the steps 7) and 8) till all reciprocal vectors on the reciprocal plane are marked, wherein the integer indices of the crystal reciprocal vectors relative to the two-dimensional grid at this time represents the reasonable geometric relationship of the crystal reciprocal vectors on the reciprocal plane.

Beneficial effects of the present invention are as follows.

The prior art utilizes EBSD diffraction geometry to geometrically correct reciprocal vectors corresponding to the Kikuchi bands in EBSD pattern. The geometric correction is capable of improving the accuracy of the angles between reciprocal vectors, but is unable to correct measurement errors. The length of reciprocal vectors is relevant with the width of the Kikuchi bands. Due to the contrast at the edges of the Kikuchi bands in EBSD patterns has poor quality, the measurement error is large. Therefore, even geometrically corrected, the geometric relationships among the reciprocal vectors are still not clear. In addition, to disclose the geometric relationships among the reciprocal vectors on the two-dimensional reciprocal plane, based on geometric correction, the prior art describes the geometric relationships among the reciprocal vectors by a one-time two-dimensional fitting method (reference: L. L. Li and M. Han. *Determining the Bravais lattice using a single electron backscatter diffraction pattern. J. Appl. Cryst.* 48(2015):107-115). However, under the circumstance of larger error, the one-time two-dimensional fitting method sometimes brings to unreasonable fitting results. Aiming at larger measurement error of the width of the Kikuchi bands shown in EBSD patterns, the present invention provides a step-by-step fitting method for minimally reducing the influence of the measurement error on the fitting result, thereby ensuring that the final fitting result is capable of correctly describing the two-dimensionally geometric relationships of the crystal reciprocal vectors on the reciprocal plane. The step-by-step fitting effect refers to embodiments.

BRIEF DESCRIPTION OF THE DRAWINGS

These and other objectives, features, and advantages of the present invention will become apparent from the accompanying drawings and the following detailed description. The drawings are shown and described for the purposes of further illustrating and being a part of the present invention. Embodiment of the present invention as shown in the drawings and described below is exemplary only and not intended to be limited.

DETAILED DESCRIPTION OF THE PREFERRED EMBODIMENT

To more clearly understand above objects, characteristics and advantages, the present invention is further illustrated combined with drawings and embodiments in detail.

Figure 1:
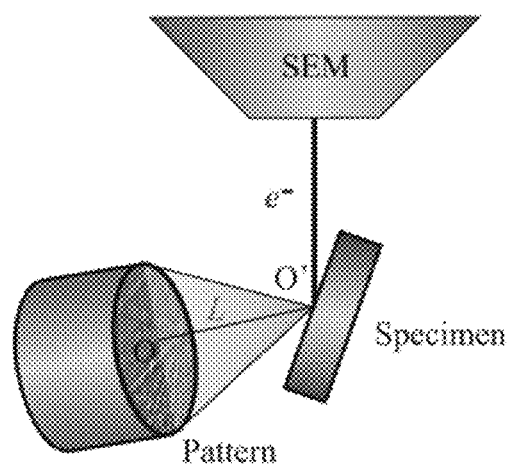
FIG. 1 is a schematic view of a SEM and an EBSD device.

Step 1): FIG. 1 is a schematic view of a SEM (scanning electron microscope) and an EBSD (electron backscattered diffraction) device, wherein the point O represents the PC (pattern center) of the EBSD, the point O' represents the signal source, and the DD (detector distance) is a ratio of L to the EBSD pattern width.

Figure 2:
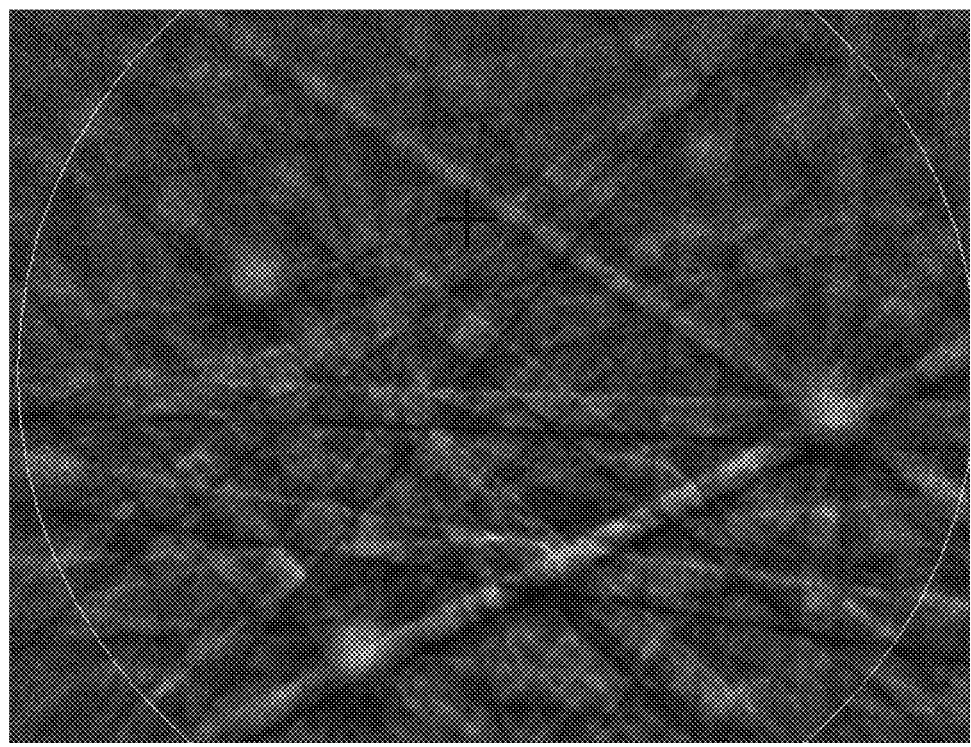
FIG. 2 shows an EBSD pattern, associated with the PC, of a mineral.

FIG. 2 shows a collected EBSD pattern of a mineral, wherein the EBSD pattern width is 237.1 mm, the black cross represents the PC used, the DD is 0.6001, the accelerating voltage U used is 15 kV, wherein the wavelength of the electron beam used is $$\lambda = \sqrt{\frac{1.5}{U(1+0.9788\times 10^{-6}U)}} = 0.009927 \text{ nm}.$$

Figure 3:
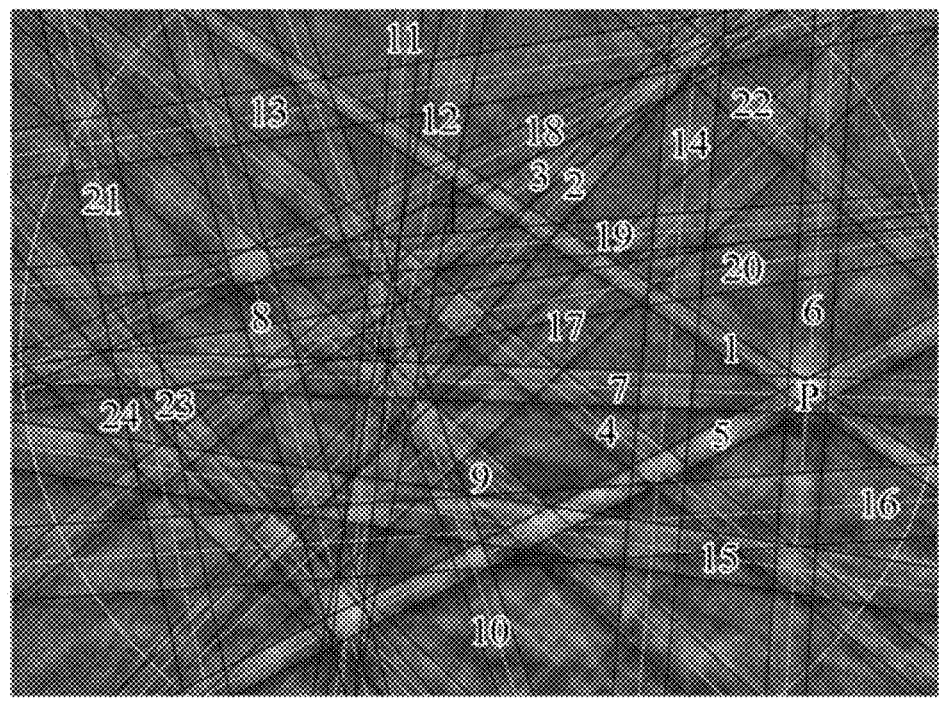
FIG. 3 shows central lines and the narrowest widths of all visible Kikuchi bands in the EBSD pattern.

Step 2): FIG. 3 shows an identification result of the EBSD pattern, wherein black parallel lines respectively represent the narrowest width of all detected Kikuchi bands in the EBSD pattern, the grey lines between the parallel lines are the central lines of the corresponding Kikuchi bands, wherein the numbers shown in FIG. 2 represent sequence numbers of the visible Kikuchi bands, and measured widths of the Kikuchi bands are listed in Table 1.

TABLE 1

Widths of the Kikuchi bands and corresponding diffraction angles and lengths of the reciprocal vectors

| No. | Width (mm) | $\theta_i$ (°) | $H_i$ (nm$^{-1}$) |
|---|---|---|---|
| 1 | 5.816 | 1.178 | 4.143 |
| 2 | 9.567 | 1.892 | 6.654 |
| 3 | 8.916 | 1.776 | 6.246 |
| 4 | 9.940 | 1.955 | 6.875 |
| 5 | 7.422 | 1.105 | 3.887 |
| 6 | 10.16 | 1.423 | 5.004 |
| 7 | 9.619 | 1.745 | 6.138 |
| 8 | 10.70 | 1.893 | 6.660 |
| 9 | 12.19 | 2.203 | 7.750 |
| 10 | 8.587 | 1.676 | 5.896 |
| 11 | 7.131 | 1.396 | 4.909 |
| 12 | 11.10 | 2.230 | 7.845 |
| 13 | 13.25 | 2.546 | 8.959 |
| 14 | 13.44 | 2.327 | 8.186 |
| 15 | 12.45 | 1.913 | 6.730 |
| 16 | 19.22 | 2.822 | 9.929 |
| 17 | 16.04 | 2.960 | 10.42 |
| 18 | 8.667 | 1.743 | 6.130 |
| 19 | 9.010 | 1.800 | 6.330 |
| 20 | 11.99 | 2.312 | 8.135 |
| 21 | 11.50 | 1.695 | 5.963 |
| 22 | 10.85 | 1.766 | 6.212 |
| 23 | 10.11 | 1.455 | 5.117 |
| 24 | 15.72 | 2.144 | 7.543 |

Figure 4:
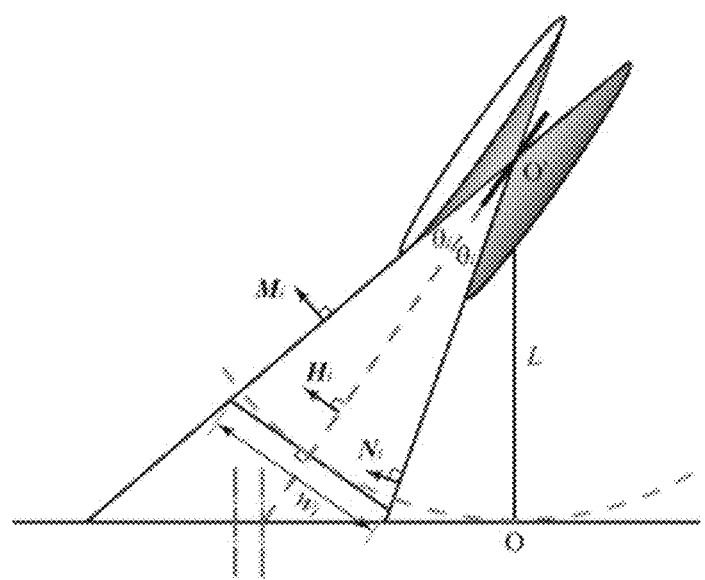
FIG. 4 is a schematic illustration of formation of a Kikuchi band.

Step 3): FIG. 4 illustrates formation principle of a Kikuchi band in the EBSD pattern, wherein the horizontal line represents the EBSD pattern plane, the intersection between two diffraction cones at the point O' and the pattern plane are the edges of the Kikuchi band; the dot dash line on the left side represents the central line of the Kikuchi band, and the dot dash line on the right side represents the trace line of the Kikuchi band; the dashed line from the point O' to the pattern plane represents a diffracting plane of the crystal, and the normal $H_i$ is directed along the direction of a reciprocal vector corresponding to the Kikuchi band; L is obtained according to the DD used and the pattern width, wherein $L = (\text{pattern width}) \times DD = 237.1 \times 0.6001 = 142.3 \text{ mm}.$ The position of the signal source is determined by the PC and the L, the angle $2\theta_i$ between planes $M_i$ and $N_i$ is determined according to the position of the signal source and the parallel lines matching with the narrowest edges of the Kikuchi bands, and the calculated diffraction angles $\theta_i$ of the Kikuchi bands are shown in Table 1, wherein after geometric correction, the width of the Kikuchi bands is $w_i = 2L \tan(\theta_i)$, the length of the reciprocal vectors is $$H_i = \frac{2}{\lambda}\tan(\theta_i).$$

Figure 5:
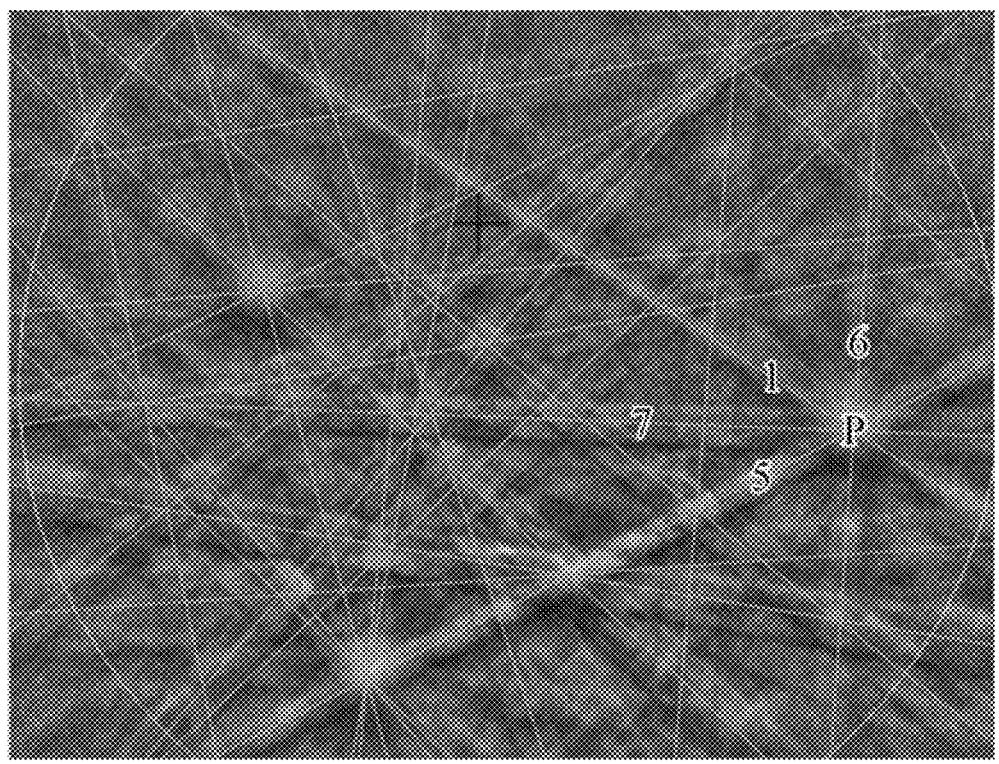
FIG. 5 is trace lines of the detected Kikuchi bands in the EBSD pattern and one Kikuchi pole indicated by P.

Table 1 also provides the length of the reciprocal vectors corresponding to the Kikuchi bands, wherein the trace line of the Kikuchi bands is determined according to an intersecting line formed by a bisector plane of planes $M_i$ and $N_i$ and the pattern plane, the trace line of the Kikuchi bands is shown in FIG. 5.

Figure 6:
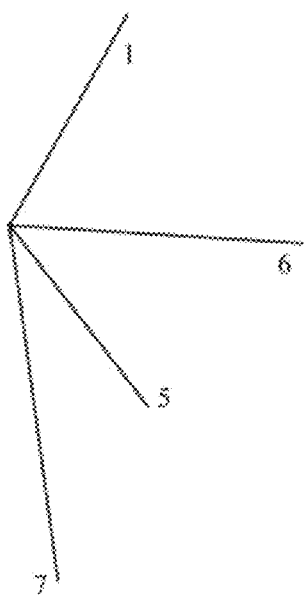
FIG. 6 is a schematic view of a two-dimensional reciprocal plane corresponding to the Kikuchi pole P.

Step 4): It can be seen from FIG. 5 that the trace lines of the Kikuchi bands 1, 5, 6 and 7 pass through the Kikuchi pole P. Therefore, the reciprocal vectors corresponding to these Kikuchi bands belong to one reciprocal plane. FIG. 6 shows the distribution of the reciprocal vectors on the reciprocal plane. Table 2 shows the coordinates of the ends of the reciprocal vectors on the two-dimensional reciprocal plane with respect to a two-dimensional Cartesian coordinate system.

TABLE 2

Coordinates of the vector ends on the reciprocal plane corresponding to the Kikuchi pole P in a two-dimensional Cartesian coordinate system and the length of the vectors

| Sequence number of reciprocal vectors | $x_i$ (nm$^{-1}$) | $y_i$ (nm$^{-1}$) | Length (nm$^{-1}$) |
|---|---|---|---|
| 1 | 2.012 | 3.621 | 4.143 |
| 5 | 2.354 | −3.094 | 3.887 |
| 6 | 4.995 | −0.3059 | 5.004 |
| 7 | 0.8299 | −6.082 | 6.138 |

Step 5): Table 3 shows the areas of the parallelograms formed by any two reciprocal vectors in FIG. 6. It can be seen that the reciprocal vectors 5 and 7 define a parallelogram with the smallest area.

TABLE 3

Areas of parallelograms formed by two reciprocal vectors

| Sequence numbers of reciprocal vectors | | Area (nm$^{-2}$) |
|---|---|---|
| 1 | 5 | 14.75 |
| 1 | 6 | 18.70 |
| 1 | 7 | 15.24 |
| 5 | 6 | 14.73 |
| 5 | 7 | 11.75 |
| 6 | 7 | 30.12 |

The reciprocal vectors 5 and 7 are selected as a two-dimensional basis, the reciprocal vector 5 is defined as $a_5$, the reciprocal vector 7 is defined as $b_7$, the angle between the reciprocal vectors 5 and 7 is defined as $\phi_{5-7}$, wherein from the coordinates of the reciprocal vectors 5 and 7 in Table 2, it can be obtained that $$a_5 = \sqrt{(2.354)^2 + (-3.094)^2} = 3.888 \text{ nm}^{-1},$$

$$b_7 = \sqrt{(0.8299)^2 + (-6.082)^2} = 6.138 \text{ nm}^{-1},$$

$$\varphi_{5-7} = \cos^{-1}\left(\frac{x_5 \times x_7 + y_5 \times y_7}{a \times b}\right) =$$

$$\cos^{-1}\left(\frac{2.354 \times 0.8299 + 3.094 \times 6.082}{3.888 \times 6.138}\right) = 29.49°,$$

the reciprocal vectors 5 and 7 are marked, and at this time only the two reciprocal vectors on the reciprocal plane are marked.

Step 6): The dotted lines in FIG. 7a form a two-dimensional grid defined by the reciprocal vectors 5 and 7. The coordinates (X, Y) of the unmarked reciprocal vectors on the reciprocal plane relative to the two-dimensional basis are determined one by one. The coordinates of the reciprocal vector 1 relative to the two-dimensional basis are set to $(X_1, Y_1)$, wherein $$\begin{cases} 2.354X_1 + 0.8299Y_1 = 2.012 \\ -3.094X_1 - 6.082Y_1 = 3.621 \end{cases}.$$

The above binary linear equation group is solved to obtain the coordinates $(X_1, Y_1)$ of the reciprocal vector 1 relative to the two-dimensional basis, that is, $(X_1, Y_1) = (1.297, -1.255)$ Similarly, the coordinates $(X_6, Y_6)$ of the reciprocal vector 6 relative to the two-dimensional basis are obtained, namely, $(X_6, Y_6) = (2.564, -1.254)$. Two nearest integers are selected to obtain relative coordinates of the reciprocal vectors 1 and 6, that is, $(1, -1)$ and $(3, -1)$ respectively.

The deviation caused by integer coordinates of the reciprocal vectors is $$D_i = \sqrt{(\Delta X_i \cdot a_5)^2 + (\Delta Y_i \cdot b_7)^2 + 2(\Delta X_i \cdot a_5)(\Delta Y_i \cdot b_7)\cos\phi_{5-7}},$$

wherein i is the sequence number of the reciprocal vectors, $\Delta X_i = X_i$-integer coordinate of X, $\Delta Y_i = Y_i$-integer coordinate of Y, the deviation of the reciprocal vector 1 is $$D_1 = \sqrt{(0.297 \times a_5)^2 + (-0.255 \times b_7)^2 + 2(0.297 \times a_5)(-0.255 \times b_7)\cos\varphi_{5-7}} = 0.7980 \text{ nm}^{-1},$$

the deviation of the reciprocal vector 6 is $$D_6 = \sqrt{(-0.436 \times a_5)^2 + (-0.254 \times b_7)^2 + 2(-0.436 \times a_5)(-0.254 \times b_7)\cos\varphi_{5-7}} = 3.147 \text{ nm}^{-1}.$$

Step 7): Due to $D_1 < D_6$, the reciprocal vector 1 should be marked, the lengths of the two-dimensional basis and the angle between the basis should be fitted again according to all the marked vectors, the new coordinates of the basis $a_{51}$ and $b_{71}$ in the Cartesian coordinate system are respectively set to $(x_{a51}, y_{a51})$ and $(x_{b71}, y_{b71})$. Using the coordinates of the marked reciprocal vectors relative to the basis and the integer coordinates of the marked reciprocal vectors relative to the Cartesian coordinate system, an overdetermined equation group can be established as follows:

$$\begin{cases} x_{a51} = x_5 = 2.354 \\ y_{a51} = y_5 = -3.094 \\ x_{b71} = x_7 = 0.8299 \\ y_{b71} = y_7 = -6.082 \\ x_{a51} - x_{b71} = x_1 = 2.012 \\ y_{a51} - y_{b71} = y_1 = 3.621 \end{cases}.$$

A least-squares solution of the above quaternary linear overdetermined equation group is $$\begin{cases} x_{a51} = 2.517 \\ y_{a51} = -2.883 \\ x_{b71} = 0.6673 \\ y_{b71} = -6.293 \end{cases}.$$

The fitting lengths of $a_{51}$ and $b_{71}$ are respectively $$a_{51} = \sqrt{(2.517)^2 + (-2.883)^2} = 3.827 \text{ nm}^{-1},$$

$$b_{71} = \sqrt{(0.6673)^2 + (-6.293)^2} = 6.328 \text{ nm}^{-1},$$

The fitting angle $\phi_{51-71}$ is $$\varphi_{51-71} = \cos^{-1}\left(\frac{2.517 \times 0.6673 + 2.883 \times 6.293}{3.827 \times 6.328}\right) = 35.06°.$$

Figure 7:
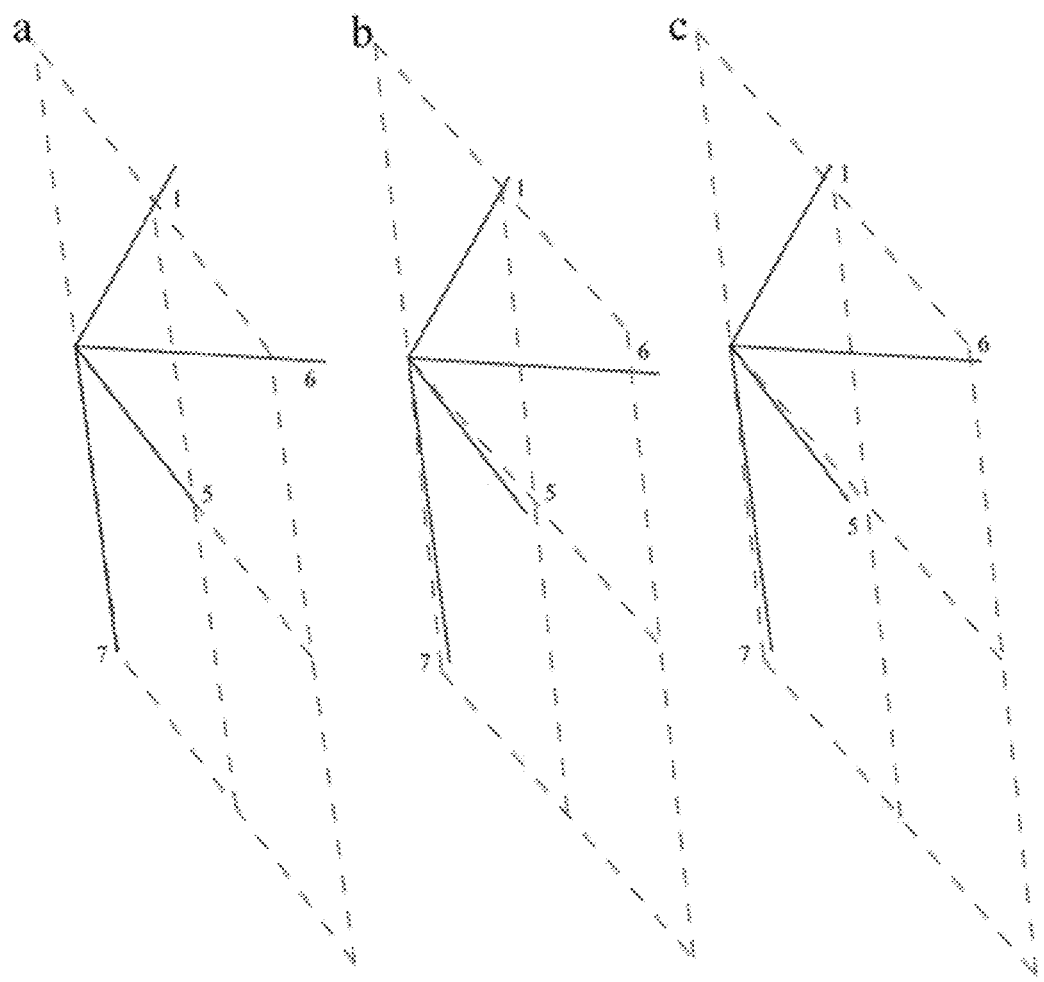
FIG. 7 shows two-dimensional grids representing geometric relationships among the reciprocal vectors on the two-dimensional reciprocal plane corresponding to the Kikuchi pole P, wherein 7a shows a two-dimensional grid defined by reciprocal vectors 5 and 7; 7b shows a two-dimensional grid after fitting based on reciprocal vectors 5, 7, and 1; and 7c shows a two-dimensional grid after fitting based on reciprocal vectors 5, 7, 1, and 6.

FIG. 7b shows a new two-dimensional grid fitted by three marked reciprocal vectors 1, 5 and 7.

Step 8): The coordinates of the reciprocal vector 6 relative to the newly fitted two-dimensional basis are set to $(X_{62}, Y_{62})$, wherein $$\begin{cases} 2.517X_{62} + 0.6673Y_{62} = 4.995 \\ -2.883X_{62} - 6.293Y_{62} = -0.3059 \end{cases}.$$

The above binary linear equation group is solved to obtain the coordinates of the reciprocal vector 6 relative to the fitted basis 5 and 7, namely, $(X_{62}, Y_{62}) = (2.244, -0.9795)$. The nearest integers are selected to obtain the coordinates $(2, -1)$.

The deviation of the reciprocal vector 6 from the nearest grid node is $$D_{62} = \sqrt{\begin{array}{c}(0.2440 \times 3.827)^2 + (0.02050 \times 6.328)^2 + \\ 2(0.2440 \times 3.827)(0.02050 \times 6.328)\cos(35.06°)\end{array}} = 1.043 \text{ nm}^{-1}$$

Similarly, the deviation of the reciprocal vector 1 can be obtained, namely, $$D_{12} = \sqrt{\begin{array}{c}(0.0835\times3.827)^2+(-0.07179\times6.328)^2+\\2(0.08351\times3.827)(-0.07179\times6.328)\cos(35.06°)\end{array}} = 0.2661 \text{ nm}^{-1}$$

The reciprocal vector 6 is marked. Up to now, all reciprocal vectors on the reciprocal plane are marked. By integer coordinates (X, Y) of the four reciprocal vectors relative to the basis, and the coordinates (x, y) of the four reciprocal vectors relative to the Cartesian coordinate system, the coordinates of the basis a and b in the Cartesian coordinate system are fitted again. A quaternary linear overdetermined equation group can be established as follows:

$$\begin{cases} x_{a52} = x_5 = 2.354 \\ y_{a52} = y_5 = -3.094 \\ x_{b72} = x_7 = 0.8299 \\ y_{b72} = y_7 = -6.082 \\ x_{a52} - x_{b72} = x_1 = 2.012 \\ y_{a52} - y_{b72} = y_1 = 3.621 \\ 2x_{a52} - x_{b72} = x_6 = 4.995 \\ 2y_{a52} - y_{b72} = y_6 = -0.3059 \end{cases}$$

A least-squares solution of the above quaternary linear overdetermined equation group is $$\begin{cases} x_{a52} = 2.726 \\ y_{a52} = -3.161 \\ x_{b72} = 0.6673 \\ y_{b72} = -6.293 \end{cases}$$

The fitting lengths of $a_{52}$ and $b_{72}$ are respectively $$a_{52} = \sqrt{(2.726)^2 + (-3.161)^2} = 4.174 \text{ nm}^{-1},$$

$$b_{72} = \sqrt{(0.6673)^2 + (-6.293)^2} = 6.328 \text{ nm}^{-1}.$$

The fitting angle $\phi_{52-72}$ is $$\varphi_{52-72} = \cos^{-1}\left(\frac{2.726\times0.6673+3.161\times6.293}{4.174\times6.328}\right) = 34.72°.$$

The coordinates of the reciprocal vector 1 relative to the fitted two-dimensional basis $a_{52}$ and $b_{72}$ are set to $(X_{13}, Y_{13})$, wherein $$\begin{cases} 2.726X_{13} + 0.6673Y_{13} = 2.012 \\ -3.161X_{13} - 6.293Y_{13} = 3.621 \end{cases}.$$

The above binary linear equation group is solved to obtain the coordinates of the reciprocal vector 1 relative to the fitted basis $a_{52}$ and $b_{72}$, namely, $(X_{13}, Y_{13})=(1.002, -1.079)$. The nearest integers are selected to obtain the coordinates of (1, −1).

The deviation of the reciprocal vector 1 from the fitting grid is $$D_{13} = \sqrt{\begin{array}{c}(0.0020\times4.174)^2+(-0.0790\times6.328)^2+\\2(0.0020\times4.174)(-0.0790\times6.328)\cos(34.72°)\end{array}} = 0.4931 \text{ nm}^{-1}$$

The deviation of the reciprocal vector 6 can be obtained at this time with the same method, namely, $$D_{63} = \sqrt{\begin{array}{c}(0.0757\times4.174)^2+(0.0060\times6.328)^2+\\2(0.0757\times4.174)(0.0060\times6.328)\cos(34.72°)\end{array}} = 0.3479 \text{ nm}^{-1}$$

The final fitting result is shown in FIG. 7c.

In the embodiment, there are four reciprocal vectors with respective sequence numbers 1, 5, 6, and 7 on the reciprocal plane P. The reciprocal vectors 5 and 7 are firstly selected as a set of two-dimensional basis, and at this time the deviations of the reciprocal vectors 1 and 6 from the two-dimensional grid nodes are respectively $D_1=0.7980$ nm$^{-1}$ and $D_6=3.147$ nm$^{-1}$. After first two-dimensional fitting, the integer coordinates of the reciprocal vector 6 relative to the basis are (3, −1), the deviations of the reciprocal vectors 1 and 6 from the fitting grid nodes are reduced to $D_{12}=0.2661$ nm$^{-1}$ and $D_{62}=1.043$ nm$^{-1}$, which can be achieved by the prior art. After second fitting, the integer coordinates of the reciprocal vector 6 relative to the basis are (2, −1), the deviations of the reciprocal vectors 1 and 6 are further changed into $D_{13}=0.4931$ nm$^{-1}$ and $D_{63}=0.3479$ nm$^{-1}$. Compared the first fitting result with the second fitting result, it can be seen that the total deviation after one by one fitting is even smaller, namely, the multiple fittings are capable of ensuring that integer coordinates (2, −1) of the reciprocal vector 6 relative to the basis are more reasonable. As mentioned above, correctly describing two-dimensionally geometric relationships of the reciprocal vectors on the reciprocal plane is a necessary prerequisite for determining Bravais lattice of unknown crystals. Due to ambiguous contrast at edges of the Kikuchi bands in EBSD patterns, the widths and the directions of the Kikuchi bands always have obvious measurement errors, indicating that the crystal reciprocal vectors are of obvious errors. The multiple fitting method provided by the present invention is capable of effectively solving the problem. Under the condition of obvious reciprocal vector errors, the two-dimensional grid with smallest total deviation is obtained. Therefore, using the step-by-step fitting method and the final two-dimensional grid, the inherent two-dimensionally geometric relationships of crystal reciprocal vectors in EBSD patterns can be correctly described.

One skilled in the art will understand that the embodiment of the present invention as shown in the drawings and described above is exemplary only and not intended to be limited.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for determining geometric relationships of crystal reciprocal vectors on two-dimensional planes obtained from single EBSD (electron back-scattered diffraction) pattern, comprising steps of:

1) collecting an EBSD pattern of a crystalline sample on a SEM (scanning electron microscope), recording the PC (pattern center), the DD (detector distance) and the accelerating voltage of the EBSD pattern;
2) identifying a pair of edges at the narrowest location for each visible Kikuchi band, determining the central line and the width of the visible Kikuchi bands on the EBSD pattern;
3) geometrically correcting all the detected Kikuchi bands by the PC and the DD for obtaining the reciprocal vectors corresponding to the Kikuchi bands, and simultaneously transforming the central line of the Kikuchi bands into the trace line of the diffracting crystal planes;
4) according to the fact which all Kikuchi bands belonging to a zone axis must pass through a Kikuchi pole, judging the relationship between the Kikuchi bands and the Kikuchi pole in order to obtain all reciprocal vectors on a reciprocal plane;
5) calculating the area of all possible parallelograms defined by any two different reciprocal vectors on a two-dimensional reciprocal plane, selecting a set of reciprocal vectors with the smallest parallelogram area as a two-dimensional basis, setting the basis as marked reciprocal vectors on the reciprocal plane;
6) according to a two-dimensional grid defined by the basis, indexing coordinates of other reciprocal vectors on the reciprocal plane with respect to the two-dimensional basis, obtaining deviations of ends of the other reciprocal vectors from the nearest grid node;
7) selecting a reciprocal vector with the smallest deviation from all unmarked reciprocal vectors on the reciprocal plane, marking the reciprocal vector with the smallest deviation, fitting the lengths and the angle of the two-dimensional basis according to the ends of the marked reciprocal vectors and the integer coordinates relative to the two-dimensional basis, redefining a two-dimensional grid by the fitting result;
8) obtaining the integer coordinates of unmarked reciprocal vectors on the reciprocal plane relative to the new two-dimensional basis, obtaining the deviation of the ends of the unmarked reciprocal vectors from the nearest grid nodes; and
9) repeating the steps 7) and 8) till all reciprocal vectors on the reciprocal plane are marked, wherein the integer indices of the crystal reciprocal vectors relative to the two-dimensional grid at this time represents the reasonable geometric relationships of the crystal reciprocal vectors on the reciprocal plane.

2. The method, as recited in claim 1, wherein in the step 2), the central line of the Kikuchi bands is firstly determined, and then a pair of parallel lines is used to respectively match with the edges at the narrowest location of the Kikuchi band, the interval between the parallel lines represents the bandwidth of the Kikuchi bands on the EBSD pattern.

3. The method, as recited in claim 1, wherein in the step 2), a pair of parallel lines are used to respectively match with the edges at the narrowest location of the Kikuchi band, the interval between the parallel lines represents the bandwidth of the Kikuchi band and the central line of the Kikuchi bands is determined according to the parallel lines.

4. The method, as recited in claim 1, wherein the step 3) specifically comprises sub-steps of:
3.1) determining L according to the DD and the EBSD pattern width, wherein $$L = (\text{EBSD pattern width}) \times DD,$$

wherein the L is a distance from a signal source to the PC of the EBSD pattern;
3.2) determining a position of the signal source according to the PC and the L;
3.3) according to the position of the signal source and the parallel lines respectively matching with the edges at the narrowest location of the Kikuchi bands, determining the angle $2\theta_i$ between planes $M_i$ and $N_i$,
wherein after geometric correction, the width of the Kikuchi bands is $w_i = 2L \tan(\theta_i)$,
the length of the reciprocal vector is $$H_i = \frac{2}{\lambda} \tan(\theta_i);$$

and
3.4) determining the trace line of the Kikuchi bands according to the intersecting line formed by the bisector plane of planes $M_i$ and $N_i$ and the EBSD pattern plane.

* * * * *